United States Patent [19]

Kornecki et al.

[11] Patent Number: 4,931,002
[45] Date of Patent: Jun. 5, 1990

[54] PYRIDOXAL-5'-PHOSPHATE AS AN IN VITRO ANTICOAGULANT FOR WHOLE BLOOD

[75] Inventors: Elizabeth H. Kornecki; Yigal H. Ehrlich, both of S. Burlington, Vt.

[73] Assignee: The University of Vermont, Burlington, Vt.

[21] Appl. No.: 55,637

[22] Filed: May 29, 1987

[51] Int. Cl.$^5$ .................. A61K 35/14; A61K 35/18
[52] U.S. Cl. ..................................... 424/529; 435/2
[58] Field of Search ........................... 435/2; 424/101

[56] References Cited

U.S. PATENT DOCUMENTS

| | | |
|---|---|---|
| 3,527,755 | 9/1970 | Murakand et al. |
| 3,579,423 | 5/1971 | Yamane et al. |
| 3,874,384 | 4/1975 | Deindoerber et al. |
| 3,910,921 | 10/1975 | Esanu |
| 4,136,093 | 1/1979 | Bonhard et al. |
| 4,137,316 | 1/1979 | Esanu |
| 4,528,295 | 7/1985 | Tabakoff |
| 4,529,719 | 7/1985 | Tye |
| 4,605,741 | 8/1986 | Zagnoli et al. |

FOREIGN PATENT DOCUMENTS 2035765  6/1969  France.

OTHER PUBLICATIONS

Kornecki et al., Biochemical and Biophysical Research Communication, vol. 90, No. 3, pp. 963–968 (1979).
Kornecki et al., Pyridoxal Phosphate Inhibition of Platelet Function, vol. 238, pp. H54–H60 (1980).
Subbareo et al., Biochemical Pharmacology, vol. 28, pp. 531–534 (1979).
Barber et al., The Journal of Pediatrics, vol. 75, No. 3, pp. 463–478 (1969).
Hambraeus et al., Clin. Science, vol. 35, pp. 457–466, (1986).
Lumeng et al., The American Journal of Clinical Nutrition, vol. 27, pp. 326–333 (1974).
Pollard et al., Proc. Natl. Acad. Sct. U.S.A., vol. 74, No. 12, pp. 5295–5299 (1977).
Zahavi et al., Thromb Haemostas (Stuttgart), vol. 52, pp. 205–209 (1984).
Holmgren et al., The Effect of Pyridoxine on Platelet Adhestivenss in Homocystinuria, vol. 5, No. 4, pp. 402–409 (1974).
Zahavi et al., Life Sciences, vol. 35, No. 14, pp. 1497–1503 (1984).
Merck Index, Abstract, p. 7882 (1983).
Maeda et al–Brit. J. of Haematology, vol. 34 (1976), pp. 501–509.
Maeda et al–Chem. Abst., vol. 86 (1977), p. 14512f.
Zahavi et al., Chem. Abst–vol. 101 (1984), pp. 168, 183q.
Sabba Rao–Chem. Abst., vol. 91 (1979), p. 105,873u.
Kark et al.–Chem. Abst., vol. 99 (1983), 52272d.
Maeda et al.–Chem. Abst., vol. 93 (1980), p. 165,225k.

*Primary Examiner*—Sam Rosen
*Attorney, Agent, or Firm*—Ernest V. Linek; George W. Neuner

[57] ABSTRACT

The use of pyridoxal-5'-phosphate as an in vitro anticoagulant agent which retains the platelet activity of stored whole blood or stored plasma for more than about six hours is disclosed.

6 Claims, No Drawings

PYRIDOXAL-5'-PHOSPHATE AS AN IN VITRO ANTICOAGULANT FOR WHOLE BLOOD

BACKGROUND OF THE INVENTION

Whole blood is typically stored for very short periods of time prior to use, due to its rapid deterioration due to factors such as clotting, cell breakup and loss of platelet activity.

SUMMARY OF THE INVENTION

The present invention provides a method for storing whole blood and blood fractions containing platelets (e.g., plasma) so that the loss of platelet activity is reduced. Thus, surprisingly whole blood treated in accord with this invention can be stored for more than six (6) hours, and up to at least about 24 hours, without loss of platelet activity whereas previously whole blood could only be stored for up to 6 hours. In accord with the invention pyridoxal-5'-phosphate is used as an in vitro anticoagulant agent e.g., when drawing blood for storage, fractionation of blood into its useful components, and the like, where retention of platelet activity is desired.

Pyridoxal-5'-phosphate is also useful as an additive to whole blood and blood fractions containing platelets, to preserve the activity of platelets for long periods of time.

DETAILED DESCRIPTION OF THE PREFERRED EMBODIMENTS

It has been discovered that pyridoxal-5'-phosphate (PLP) provides excellent anticoagulant properties during the collection of whole blood.

It has further been discovered that the inhibition of blood clotting afforded by PLP lasts for a long period of time (e.g., greater than 24 hr.).

Finally, it has been discovered that the inhibition of coagulation by PLP is a reversible process, since washed platelets, when resuspended in PLP-free Tyrodes Buffer, were able to aggregate normally when exposed to ADP and thrombin, indicating that no permanent platelet functional damage had occurred due to exposure to PLP for up to 24 hours at room temperature.

PLP is a naturally occurring derivative of vitamin $B_6$ which has previously been reported as an inhibitor of ADP and thrombin-induced platelet aggregation in both platelet—rich plasma and in a washed platelet system. See for example, Kornecki et al., *Amer. J. Physiol.*, 238: H54–60 (1980) and Kornecki et al., *Biochem. Biophys. Res. Commun.*, 90: 963–968 (1979).

While there has been at least one previous study reporting that PLP can act as both an in vitro and in vivo plasma anticoagulant (see, Subbarao et al., *Biochem. Pharmacol.*, 28: 531–534 (1979)), the present inventors are aware of no reports which suggest that PLP be used for the collection and/or storage of whole blood and, particularly, no reports that suggest that when using PLP as an anticoagulant for the storage of whole blood, plasma or platelets, there is no loss of platelet activity for at least 24 hours at room temperature. Prolonging of platelet activity can be further increased by lowering the temperature of the material.

In fact, the findings reported herein were quite surprising to the present inventors, given the well known problems associated with conventional anticoagulants used for blood collection.

Typical anticoagulants for blood collection (or its components, e.g., plasma) include acid citrate dextrose (ACD); citrate phosphate dextrose (CPD); citrate phosphate dextrose adenine (CPD-A); sodium citrate and EDTA, which either decrease the pH of the collected blood or chelate essential divalent ions such as $Ca^{2+}$, $Mg^{2+}$, and the like. Heparin, another widely used anticoagulant, has been shown to aggregate platelets in certain cases. Changes in blood pH and/or prolonged chelation of essential ions, is known to cause irreversible damage to the blood cells, especially platelets, due to the disruption of major membrane protein complexes.

In contrast to the aforementioned problems, the use of the water-soluble vitamin $B_6$ derivative, PLP, at neutral pH, neither changes the blood pH, nor acts to cause irreversible damage to platelets, thereby avoiding the problems of the prior art compounds.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLE I

| CONCENTRATIONS OF PYRIDOXAL-5'-PHOSPHATE TESTED FOR THEIR ANTICOAGULANT ACTIVITY | |
|---|---|
| FINAL CONCENTRATION OF PLP | CLOTTING OF WHOLE BLOOD |
| 0 PLP | Clot forms in 13 min. |
| 0.1 mM PLP* | Clot forms in 18 min. |
| 0.3 mM PLP | Clot forms in 18 min. |
| 0.5 mM PLP | Clot forms in 18 min. |
| 1 mM PLP | Clot forms in 20 min. |
| 2 mM PLP | Clot forms in 24 min. |
| 4 mM PLP | No Clotting |
| 5 mM PLP | No clotting |

*In Example I, a freshly prepared aqueous stock solution of pyridoxal - 5' - phosphate was prepared as a 50 mM aqueous solution, pH 7.4, containing 2.23% dextrose. The concentrations of PLP were final.

EXAMPLE II

| EFFECT OF 5.5 mM PYRIDOXAL-5'-PHOSPHATE ON THE INHIBITION OF CLOTTING OF WHOLE BLOOD | |
|---|---|
| Time of Incubation of Whole Blood with 5.5 mM PLP | Clotting of Whole Blood |
| 12 hr. | NO |
| 24 hr. | NO |

In this Example, whole blood was collected into 50 cc tubes containing 4 ml of an aqueous stock solution of PLP. The final concentration of PLP was 5.5 mM. The tubes were capped and mixed at room temperature for either a 12 hour or a 24 hour period by use of an aliquot mixer.

EXAMPLE III

| EFFECT OF THE ADDITION OF PLP PLUS CPDA ON THE CLOTTING OF BLOOD | |
|---|---|
| COMPOUNDS TESTED | Clotting of Whole Blood? |
| PLP (5.5 mM) | NO |
| PLP (5.5 mM) plus CPDA-1* | NO |
| CPDA-1* | NO |

*In this Example, the CPDA-1 solution was the commercially available blood anticoagulant obtained from Fenwal Laboratories, a division of Travenol Laboratories, Deerfield, IL.

A 63 ml aqueous solution of this USP grade CPDA-1 contained the following: 206 mg citric acid, 1.66 g sodium citrate, 140 mg monobasic sodium phosphate, 2 g dextrose and 17.3 mg adenine. The ratio (v/v) of the CPDA-1 solution to whole blood was 1:7.14.

EXAMPLE IV

| INHIBITION OF CLOTTING OF PLASMA BY PYRIDOXAL-5'-PHOSPHATE | |
|---|---|
| Plasma Contained the following: | Clotting in 24 hr |
| Control (No PLP) | Yes |
| PLP (5.5 mM) | No |
| PLP (5.5 mM) plus CPDA-1* | No |
| CPDA-1* | No |

*In this Example, the CPDA-1 solution was the commercially available blood anticoagulant obtained from Fenwal Laboratories, a division of Travenol Laboratories, Deerfield, Il.

A 63 ml aqueous solution of this USP grade CPDA-1 contained the following: 206 mg citric acid, 1.66 g sodium citrate, 140 mg monobasic sodium phosphate, 2 g dextrose and 17.3 mg adenine. The ratio (v/v) of the CPDA-1 solution to plasma was 1:7.14.

EXAMPLE V

PREPARATION AND TESTING OF PLATELET FUNCTIONAL PROPERTIES IN GEL-FILTERED PLATELETS OBTAINED FROM FRESH WHOLE BLOOD ANTICOAGULATED IN THE PRESENCE OF 5.4 mM PYRIDOXAL-5'-PHOSPHATE

| | Platelet Aggregation Parameters* | |
|---|---|---|
| Agonists Tested | Initial Velocity (LTU/min) | Extent (LTU) |
| ADP (49 uM) | 96 | 62 |
| ADP (20.8 uM) | 84 | 66 |
| Collagen (111 ug/ml) | 29 | 78 |
| Thrombin (5.5 U/ml) | 120 | 70 |
| A23187 (35 uM) | 36 | 76 |
| PAF (24.5 uM) | 74 | 54 |
| PAF (1.64 uM) | 68 | 54 |
| PAF (326 nM) | 92 | 64 |
| PAF (164 nM) | 84 | 64 |
| PAF (20.2 nM) | 68 | 56 |
| PAF (10.2 nM) | 13 | 9 |

*For Examples V-IX, the procedures of Kornecki et al., Science, 226: 1454–1456 (1984) were followed for the preparation of gel-filtered platelets and for aggregation of 0.45 ml aliquots of platelets.

Platelet aggregation was initiated by the addition of the agonists described above. The concentrations shown above were final.

EXAMPLE VI

PREPARATION AND TESTING OF THE PLATELET FUNCTIONAL PROPERTIES IN GEL-FILTERED PLATELETS OBTAINED FROM WHOLE BLOOD ANTICOAGULATED IN THE PRESENCE OF PLP (5.4 mM) PLUS CDPA-1*

| | Platelet Aggregation Parameters** | |
|---|---|---|
| Agonist Tested | Initial Velocity (LTU/min) | Extent (LTU) |
| ADP (49 uM) | 44 | 46 |
| ADP (20.8 uM) | 54 | 60 |
| Collagen (111 ug/ml) | 28 | 66 |
| Thrombin (5.5 U/ml) | 76 | 68 |
| A23187 (35 uM) | 24 | 78 |
| PAF (24.5 uM) | 52 | 42 |
| PAF (1 um) | 27 | 28 |
| PAF (20.2 nM) | 14 | 14 |

*In this Example, the CDPA-1 solution was the commercially available blood anticoagulant obtained from Fenwal Laboratories, a division of Travenol Laboratories, Deerfield, Il.
**See Example V.

A 63 ml aqueous solution of this USP grade CPDA-1 contained the following: 206 mg citric acid, 1.66 g sodium citrate, 140 mg monobasic sodium phosphate, 2 g dextrose and 17.3 mg adenine. The ratio (v/v) of the CPDA-1 solution to the whole blood was 1:7.14.

EXAMPLE VII

PREPARATION AND TESTING OF PLATELET FUNCTIONAL PROPERTIES IN GEL-FILTERED PLATELETS FROM 24 HR-OLD BLOOD ANTICOAGULATED IN THE PRESENCE OF 5.4 mM PLP

| | Platelet Aggregation Parameters* | |
|---|---|---|
| Agonist Tested | Initial Velocity (LTU/min) | Extent (LTU) |
| ADP (49 uM) | 40 | 44 |
| ADP (20.8 uM) | 44 | 54 |
| Collagen (111 ug/ml) | 19 | 48 |
| Thrombin (5.5 U/ml) | 44 | 48 |
| A23187 (35 uM) | 32 | 50 |
| PAF (24.5 uM) | 36 | 40 |
| PAF (20 nM) | 12 | 18 |

*See Example V.

EXAMPLE VIII

RESPONSIVENESS OF GEL-FILTERED PLATELETS PREPARED FROM PLASMA KEPT ANTICOAGULATED FOR 24 HOURS IN THE PRESENCE OF PLP (5.4 mM): COMPARISON WITH CPDA-1*

| | Extent of Platelet Aggregation (LTU)** | |
|---|---|---|
| Agonists Tested | Pyridoxal-5'-Phosphate as anticoagulant | CPDA-1* as anticoagulant |
| ADP (49 uM) | 54 | 8 |
| PAF (20 nM) | 26 | 0 |
| Collagen (111 ug/ml) | 58 | 0 |
| Thormbin (5.5 U/mL) | 58 | 14 |

*In this Example, the CPDA-1 solution was the commercially available blood anticoagulant obtained from Fenwal Laboratories, a division of Travenol Laboratories, Deerfield, Il.
**See Example V.

A 63 ml aqueous solution of this USP grade CPDA-1 contained the following: 206 mg citric acid, 1.66 g sodium citrate, 140 mg monobasic sodium phosphate, 2 g dextrose and 17.3 mg adenine. The ratio (v/v) of the CPDA-1 solution to the whole blood was 1:7.14.

EXAMPLE IX

THE EFFECT OF THE ADDITION OF PLP TO CPDA-1: RESPONSIVENESS OF GEL-FILTERED PLATELETS ISOLATED FROM PLASMA STORED FOR 24 HR. IN THE PRESENCE OF PLP (5.4 mM) PLUS CPDA-1*

| Agonists Tested | Extent of Platelet Aggregation (LTU)** | | | |
|---|---|---|---|---|
| | PLP | CPDA-1 | PLP plus CPDA-1 | % Recovery by the addition of PLP to CPDA-1 |
| ADP (49 uM) | 54 | 8 | 74 | >100 |
| PAF (20 nM) | 26 | 0 | 22 | 85 |
| Collagen (111 ug/ml) | 58 | 0 | 90 | >100 |
| Thrombin (5.5 U/ml) | 58 | 14 | 50 | 86 |

*In this Example, the CPDA-1 solution was the commercially available blood anticoagulant obtained from Fenwal Laboratories, a division of Travenol Laboratories, Deerfield, Il.
**See Example V.

A 63 ml aqueous solution of this USP grade CPDA-1 contained the following: 206 mg citric acid, 1.66 g sodium citrate, 140 mg monobasic sodium phosphate, 2 g dextrose and 17.3 mg adenine. The ratio (v/v) of the CPDA-1 solution to the plasma was 1:7.14.

The following are some of the conclusions that can be drawn from the foregoing examples:

1. Pyridoxal-5'-phosphate (PLP) at concentrations of about 4 mM and greater, can be used as an effective anticoagulant of whole blood (see Example I), without loss of platelet activity for up to 24 hours.
2. Pyridoxal-5'-phosphate, when added to whole blood, can be used for the purpose of long-term storage of whole blood (at least over a 24-hour period of time) (see Example II).
3. Pyridoxal-5'-phosphate can be used as an "additive" combined with conventional anticoagulants used in blood banks, such as CPDA-1 (see Example III), thereby reducing the loss of platelet activity experienced when using such anticoagulants alone.
4. Plasmas which were obtained from whole blood collected in tubes containing either (a) PLP, (b) the standard anticoagulant used in blood banks, CPDA-1, or (c) a combination of PLP plus CPDA, did not exhibit any clotting over a 24 hr. incubation period. (see Example IV).
5. Platelets, which were isolated from whole blood anticoagulated in the presence of PLP (5.4 mM), exhibited responsiveness to all platelet agonists tested. (see Example V).
6. Platelets which were isolated from whole blood anticoagulated in the presence of both PLP (5.4 mM) plus CPDA-1, exhibited responsiveness to all platelet agonists. (see Example VI).
7. Platelets, which were isolated from 24 hr. old whole blood anticoagulated in the presence of PLP, exhibited responsiveness to all platelet agonists. (see Example VII).
8. Platelets isolated from platelet-rich plasma, which was kept for 24 hr. with pyridoxal-5'-phosphate, showed responsiveness to all physiological agonists tested. (see Example VIII).
9. Platelets isolated from platelet-rich plasma, which was kept for 24 hr. with CPDA-1, showed loss in responsiveness to physiological agonists. (see Example VIII).
10. Preservation of platelet responsiveness may be accomplished by the use of PLP as an additive to traditional anticoagulants, such as CPDA-1. (see Example IX).

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. In vitro stored whole blood containing pyridoxal-5'-phosphate in a concentration of at least about 4.0 mM, said whole blood retaining platelet activity for at least six (6) hours.

2. A method of preparing whole blood for storage, without loss of platelet activity during said storage, for periods of more than six (6) hours, said method comprising treating the whole blood to be stored by adding pyridoxal-5'-phosphate at a concentration of about 4 mM or greater, thereby reducing the loss of platelet activity during storage.

3. The method of claim 2, further comprising storing the treated whole blood for more than 6 hours before use.

4. The method of claim 2, further comprising storing the treated whole blood for more than 24 hours before use.

5. The method of claim 2, 3 or 4, further comprising adding a conventional anticoagulant to the whole blood.

6. The method of claim 5, wherein the conventional anticoagulant comprises sodium citrate.

* * * * *